US008927610B2

(12) United States Patent
Clomburg, Jr. et al.

(10) Patent No.: US 8,927,610 B2
(45) Date of Patent: Jan. 6, 2015

(54) PROCESS FOR THE PRODUCTION OF METHANE

(75) Inventors: Lloyd Anthony Clomburg, Jr., Houston, TX (US); Anand Nilekar, Houston, TX (US)

(73) Assignee: Shell Oil Company, Houston, TX (US)

( * ) Notice: Subject to any disclaimer, the term of this patent is extended or adjusted under 35 U.S.C. 154(b) by 343 days.

(21) Appl. No.: 13/388,307

(22) PCT Filed: Aug. 2, 2010

(86) PCT No.: PCT/US2010/044063
§ 371 (c)(1),
(2), (4) Date: Mar. 22, 2012

(87) PCT Pub. No.: WO2011/017242
PCT Pub. Date: Feb. 10, 2011

(65) Prior Publication Data
US 2012/0178833 A1    Jul. 12, 2012

Related U.S. Application Data

(60) Provisional application No. 61/230,778, filed on Aug. 3, 2009.

(51) Int. Cl.
*C07C 27/00* (2006.01)
*C07C 1/04* (2006.01)

(52) U.S. Cl.
CPC .............. *C07C 1/0435* (2013.01); *C07C 1/0485* (2013.01); *C07C 1/041* (2013.01); *C07C 2523/755* (2013.01)
USPC ........... 518/700; 702/703; 702/704; 702/705; 702/706; 702/715

(58) Field of Classification Search
USPC .......... 518/700, 702, 703, 704, 705, 706, 715
See application file for complete search history.

(56) References Cited

U.S. PATENT DOCUMENTS

| | | | |
|---|---|---|---|
| 3,128,163 A | 4/1964 | Weittenhiller | |
| 3,666,682 A | 5/1972 | Muenger | |
| 3,904,389 A | 9/1975 | Banquy | |
| 3,928,001 A | 12/1975 | Child et al. | |
| 3,970,435 A | 7/1976 | Schultz | |
| 4,017,274 A | 4/1977 | Galstaun | |
| 4,046,523 A | 9/1977 | Kalina et al. ................. | 48/197 R |
| 4,134,908 A * | 1/1979 | Steiner et al. ................. | 518/715 |
| 4,208,191 A | 6/1980 | Sze | |
| 4,235,044 A | 11/1980 | Cheung | |
| 4,298,694 A | 11/1981 | Skov | |
| 4,431,751 A * | 2/1984 | Hohlein et al. ............... | 518/706 |
| 4,839,391 A | 6/1989 | Range et al. .................. | 518/712 |
| 6,755,980 B1 | 6/2004 | Van Den Born et al. ..... | 210/767 |
| 2002/0004533 A1 | 1/2002 | Wallace et al. | |
| 2002/0055545 A1 | 5/2002 | Sheppard et al. | |
| 2006/0260191 A1 | 11/2006 | Van Den Berg et al. ........ | 48/197 |
| 2007/0011945 A1 | 1/2007 | Grootveld et al. ............. | 48/197 |
| 2008/0013258 A1 | 1/2008 | Viswanathan et al. | |
| 2008/0142408 A1 | 6/2008 | Eilers et al. .................... | 208/61 |
| 2008/0172941 A1 | 7/2008 | Jancker et al. .................... | 48/73 |

FOREIGN PATENT DOCUMENTS

| | | | |
|---|---|---|---|
| CH | 499614 | 1/1971 | |
| DE | 2624396 | 12/1976 | |
| DE | 2914806 | 10/1979 | |
| DE | 2949588 | 6/1980 | |
| DE | 3121991 | 11/1985 | |
| EP | 45352 | 7/1984 | |
| EP | 0661373 | 7/1995 | ............... C10K 1/10 |
| EP | 0722999 | 7/1996 | ................ C10J 3/86 |
| EP | 1958921 | 8/2008 | |
| GB | 2018818 | 10/1979 | |
| JP | S5582188 | 6/1980 | |
| JP | S4943904 | 9/2008 | |
| WO | 9953561 | 10/1999 | |
| WO | 0073404 | 12/2000 | |
| WO | 2007025691 | 3/2007 | |
| WO | WO 2007125047 | 11/2007 | ................ C10J 3/48 |

OTHER PUBLICATIONS

Holm-Larsen, H. $Co_2$ reforming for large scale methanol plants—an actual case, Studies in Surface Science and Catalysis, vol. 136, pp. 441-446 (2001).
Kimura, Hideo, et al.; Coal Chemistry and Industry 3rd Edition published in Mar. 1, 1984, pp. 368-371.
Xu, Jianguo et al., "Methane Steam Reforming, Methanation and Water-Gas Shift; I. Intrinsic Kinetics," AIChE Journal, Jan. 1989, vol. 35, No. 1, pp. 88-96.

* cited by examiner

Primary Examiner — Jafar Parsa (57) ABSTRACT

A process for the production of methane comprising reacting at least part of a feed gas containing carbon monoxide and hydrogen in an internally cooled methanation reactor containing a nickel comprising methanation catalyst to produce a product gas containing methane, cooling the internally cooled methanation reactor with water, wherein the water enters the internally cooled methanation reactor at a temperature in the range from 20-120° C. below its boiling temperature.

14 Claims, 4 Drawing Sheets

PROCESS FOR THE PRODUCTION OF METHANE

PRIORITY CLAIM

The present application claims priority from PCT/US2010/044063, filed 2 Aug. 2010, which claims priority from U.S. provisional application 61/230,778, filed 3 Aug. 2009.

TECHNICAL FIELD OF THE INVENTION

The invention relates to a process for the production of methane.

BACKGROUND OF THE INVENTION

A methanation reaction comprises a catalytic reaction of hydrogen with carbon monoxide to produce methane. This methane is sometimes also referred to as synthetic natural gas (SNG) and can be used as substitute gas for natural gas. In areas where there is little natural gas available, other sources of energy, such as coal or petroleum coke, may be partially oxidized in a gasification process to produce a gas comprising hydrogen and carbon monoxide. Such a gas comprising hydrogen and carbon monoxide is sometimes also referred to as synthesis gas. The synthesis gas can subsequently be used to produce synthetic natural gas (SNG) in a methanation process.

The methanation reaction proceeds, in the presence of a suitable methanation catalyst, in accordance with the following equations:

$$CO + 3H_2 = CH_4 + H_2O + \text{heat} \quad (1)$$

$$CO_2 + 4H_2 = CH_4 + 2H_2O + \text{heat} \quad (2).$$

The water formed during the reaction can, depending on the catalyst, temperature and concentrations present, subsequently react in-situ with carbon monoxide in a water-gas shift reaction in accordance with the following equation:

$$CO + H_2O = CO_2 + H_2 + \text{heat} \quad (3)$$

Reaction (1) is considered the main reaction and reactions (2) and (3) are considered to be side reactions. All the reactions are exothermic.

The methanation reactions are reversible and an increasing temperature will tend to shift the equilibrium towards a lower yield. To control the temperature, the methanation reaction can be carried out in one or more internally cooled reactors, where the reactants can be cooled by a coolant.

U.S. Pat. No. 4,839,391 describes a one-stage process for the methanation of synthesis gas to generate methane and superheated steam. The methanation reactor comprises a catalyst bed with different temperature regions, through which a cooling system passes. A cooling medium, i.e. water, flows through the cooling system countercurrently to the flow of synthesis gas through the catalyst bed. In the process, the synthesis gas successively flows through an inflow region, a hot spot region and an outward gas flow region. Cooling water is converted to steam by heat transfer in the outward gas flow region and hot spot region of the reactor, also referred to as vaporizer. Subsequently the steam is being superheated in the hot spot region of the reactor, also referred to as superheater. An external heat exchanger is used to preheat the water before entering the reactor against the effluent methane/synthesis gas mixture from the reactor. In operation example 8, synthesis gas flows into a methanation reactor at a pressure of 50 bars and a temperature of 280° C. and after methanation of the synthesis gas in the methanation reactor a product gas is obtained at a pressure of 47 bars and a temperature of 350° C. Preheated cooling water of 260° C. is introduced into a steam chamber, where it is brought up to a temperature of 310° C. at a pressure of 100 bars and then introduced into the vaporizer (boiler), in which it is converted to steam at a vaporization temperature of 311° C. (the boiling temperature of water at 100 bars is about 311° C.). The steam produced is led back into the steam chamber and then flows into the superheater where it is superheated to 500° C. at 100 bars.

A disadvantage of the process of U.S. Pat. No. 4,839,391 is the high exit temperature of the product gas, which limits the conversion in the last part of the methanation reactor.

U.S. Pat. No. 4,431,751 describes a method for producing superheated steam with the heat of catalytic methanation of a synthesis gas containing carbon monoxide, carbon dioxide and hydrogen. The process passes a gas stream first through a first internally water-cooled reactor, subsequently through an adiabatic reactor and a subsequent heat exchanger and finally through a second internally water-cooled reactor. The internally water-cooled reactors comprise a cooling system disposed within a catalyst bed through which water flows. As catalyst a nickel-containing catalyst is used. Water is passed in succession, first through the cooling system of the second internally water-cooled reactor for preheating thereof to a temperature approximating the saturated steam temperature, thereafter into the first internally water-cooled reactor for conversion into saturated steam and subsequently to the heat exchanger following the adiabatic reactor for superheating. In the exemplified process the second internally water-cooled reactor is set to operate at a gas entrance temperature between 250° C. and 350° C., specifically 300° C., at an average pressure of 37.5 bar and the product gas flowing out of the second internally water-cooled reactor is 300° C. In the example the water is brought up to a pressure of 110 bar and preheated up to 160° C. before entering the cooling system of the second internally water-cooled reactor (the boiling temperature of water at 110 bars is about 318° C.). A disadvantage of the process of U.S. Pat. No. 4,431,751 is that the very low entrance temperature of the water in the second internally water-cooled reactor, especially in combination with the cooling system used, can lead to cold spots in the catalyst bed which are expected to result deactivation of the nickel catalyst due to the formation of nickel carbonyl. In addition the process of U.S. Pat. No. 4,431,751 requires an adiabatic reactor to allow the steam to become superheated.

It would be an advancement in the art to provide a process for the production of methane wherein the above disadvantages are avoided.

SUMMARY OF THE INVENTION

The above has been achieved with the process according to the invention.

Accordingly, the present invention provides a process for the production of methane comprising reacting at least part of a feed gas containing carbon monoxide and hydrogen in an internally cooled methanation reactor containing a nickel comprising methanation catalyst to produce a product gas containing methane,
cooling the internally cooled methanation reactor with water, wherein the water enters the internally cooled methanation reactor at a temperature in the range from 20-120° C. below its boiling temperature.

The process according to the invention allows a good conversion in the last part of the internally cooled methanation reactor whilst deactivation of the nickel catalyst is minimized.

BRIEF DESCRIPTION OF THE DRAWINGS

The process according to the invention is illustrated with the following drawings.

DETAILED DESCRIPTION OF THE INVENTION

The feed gas containing carbon monoxide and hydrogen, may be any gas comprising carbon monoxide and hydrogen. An example of a gas comprising carbon monoxide and hydrogen is synthesis gas. Herein synthesis gas is understood to be a gas comprising at least hydrogen and carbon monoxide. In addition, the synthesis gas may comprise other compounds such as carbon dioxide, water, nitrogen, argon and/or sulphur containing compounds. Examples of sulphur containing compounds that may be present in synthesis gas include hydrogen sulphide and carbonyl sulphide.

The synthesis gas may be obtained by reacting a carbonaceous feed and an oxidant in a gasification reaction.

By a carbonaceous feed is understood a feed comprising carbon in some form. The carbonaceous feed may be any carbonaceous feed known by the skilled person to be suitable for the generation of synthesis gas. The carbonaceous feed may comprise solids, liquids and/or gases. Examples include coal, such as lignite (brown coal), bituminous coal, sub-bituminous coal, anthracite, bitumen, oil shale, oil sands, heavy oils, peat, biomass, petroleum refining residues, such as petroleum coke, asphalt, vacuum residue, or combinations thereof. As the synthesis gas is used in a methanation process the synthesis gas is preferably obtained by gasification of a solid or liquid carbonaceous feed. In a preferred embodiment, the synthesis gas is obtained by gasification of a solid carbonaceous feed that comprises coal or petroleum coke.

By an oxidant is understood a compound capable of oxidizing another compound. The oxidant may be any compound known by the skilled person to be capable of oxidizing a carbonaceous feed. The oxidant may for example comprise oxygen, air, oxygen-enriched air, carbon dioxide (in a reaction to generate carbon monoxide) or mixtures thereof. If an oxygen-containing gas is used as oxidant, the oxygen-containing gas used may be pure oxygen, mixtures of oxygen and steam, mixtures of oxygen and carbon dioxide, mixtures of oxygen and air or mixtures of pure oxygen, air and steam.

In a special embodiment the oxidant is an oxygen-containing gas containing more than 80 vol %, more than 90 vol % or more than 99 vol % oxygen. Substantially pure oxygen is preferred. Such substantially pure oxygen may for example be prepared by an air separation unit (ASU).

In some gasification processes, a temperature moderator may also be introduced into the reactor. Suitable moderators include steam and carbon dioxide.

The synthesis gas may be generated by reacting the carbonaceous feed with the oxidant according to any method known in the art. In a preferred embodiment the synthesis gas is generated by a partial oxidation of a carbonaceous feed, such as coal or petroleum coke, with an oxygen-containing gas in a gasification reactor.

Synthesis gas leaving a gasification reactor is sometimes also referred to as raw synthesis gas. This raw synthesis gas may be cooled and cleaned in a number of subsequent cooling and cleaning steps. The total of the gasification reactor and the cooling and cleaning steps is sometimes also referred to as a gasification unit.

Examples of suitable gasification processes, reactors for such gasification processes and gasification units are described in "Gasification" by Christopher Higman and Maarten van der Burgt, published by Elsevier (2003), especially chapters 4 and 5 respectively. Further examples of suitable gasification processes, reactors and units are described in US2006/0260191, WO2007125047, US20080172941, EP0722999, EP0661373, US20080142408, US20070011945, US20060260191 and U.S. Pat. No. 6,755,980.

Preferably raw synthesis gas produced by reacting a carbonaceous feed and an oxidant in a gasification process is cooled and cleaned before using it as a feed gas in the process of the invention. The raw synthesis gas leaving a gasification reactor can for example be cooled by direct quenching with water or steam, direct quenching with recycled synthesis gas, heat exchangers or a combination of such cooling steps, to produce a cooled synthesis gas. In the heat exchangers, heat may be recovered. This heat may be used to generate steam or superheated steam. Slag and/or other molten solids that may be present in the produced synthesis gas can suitably be discharged from the lower end of a gasification reactor. Cooled synthesis gas can be subjected to a dry solids removal, such as a cyclone or a high-pressure high-temperature ceramic filter, and/or a wet scrubbing process, to produce a cleaned synthesis gas.

In a preferred embodiment, the feed gas is desulphurized before using it in the process of the invention. The preferably cooled and cleaned synthesis gas may thus be desulphurized to produce a desulphurized synthesis gas before it is used as feed gas. The desulphurization may be carried out in a desulphurizing unit where sulphur containing compounds, such as hydrogen sulphide and carbonyl sulphide, can be removed from the feed gas. Desulphurization can for example be carried out by so-called physical absorption and/or by a chemical solvent extraction process.

In addition the feed gas may be treated to reduce the carbon dioxide content of the synthesis gas.

In one advantageous embodiment sulphur containing compounds and carbon dioxide in the feed gas are removed in a combined sulphur/carbon dioxide removal unit.

In a further preferred embodiment the molar ratio of hydrogen to carbon monoxide in the feed gas is increased before use of the feed gas in the process of the invention. The molar ratio of hydrogen to carbon monoxide in the feed gas can for example be increased by reacting carbon monoxide in the feed gas with water in a water-gas shift reaction. The water-gas shift reaction can be carried out before a desulfurization of the feed gas, also referred to as a sour water-gas shift reaction, or after a desulfurization of the feed gas, also referred to as a sweet water-gas shift reaction. Preferably a water-gas shift reaction is carried out before desulfurization of the feed gas.

The water-gas shift reaction may comprise a so called high temperature water-gas shift reaction carried out at a temperature preferably above 250° C. and more preferably at a temperature in the range from 300 to 450° C. and/or a so called low temperature water-gas shift reaction, carried out at a temperature preferably below 250° C. and more preferably in the range from 150-225° C. In a preferred embodiment the molar ratio of hydrogen to carbon monoxide in the feed gas is increased before desulfurization in a high temperature water-gas shift reaction.

The water-gas shift catalyst may be any catalyst known to be suitable for such purpose. The water-gas shift catalyst may for example contain copper, zinc, iron and/or chromium, optionally in the form of oxides and/or supported by a carrier. A high temperature water-gas shift reaction is preferably carried out using a catalyst containing iron and/or chromium. A low temperature water-gas shift reaction is preferably carried out using a catalyst containing copper and/or zinc oxide.

The shifted feed gas may comprise carbon monoxide, carbon dioxide, water and hydrogen and may in addition comprise sulfur-containing compounds. In addition, the shifted feed gas may comprise other compounds such as nitrogen and argon.

Water can be removed from the shifted feed gas by any method known to be suitable for that purpose. For example, water can be removed with a flash drum, knocking out preferably at least 70 wt % or more preferably at least 90 wt % of the water. Most preferably essentially all water is removed in the flash drum.

Carbon dioxide can be removed from the shifted feed gas in an acid gas removal unit. Carbon dioxide may be removed by any method known to be suitable for that purpose. For example carbon dioxide may be removed by cryogenic cooling, or by physical absorption or in a chemical solvent extraction process.

In an especially preferred embodiment a feed gas, such as for example synthesis gas, is treated in a water-gas shift unit and subsequently sulfur-containing compounds, carbon dioxide and water are removed from it, before using it in the process of the invention.

In the process according to the invention at least part of the carbon monoxide and hydrogen in the feed gas are reacted in an internally cooled methanation reactor in the presence of a nickel comprising methanation catalyst to produce a product gas containing methane.

The internally cooled methanation reactor is cooled with water. The water enters the internally cooled methanation reactor at a temperature in the range from 20-120° C. below its boiling temperature.

By water is herein understood water in the liquid phase, in the vapour phase or in a mixture thereof. The water may for example be liquid water, steam or superheated steam.

The internally cooled methanation reactor can be any internally cooled reactor known in the art to be suitable for a methanation process. The internally cooled methanation reactor may for example comprise a fixed or fluidized catalyst bed comprising the nickel containing methanation catalyst, which catalyst bed is cooled by a cooling system comprising one or more tubes through which the water flows. In another embodiment the internally cooled methanation reactor may comprise one or more tubes containing the methanation catalyst, which tubes are cooled via a space surrounding the tubes through which water can flow.

Preferably the internally cooled reactor comprises tubes filled with a nickel containing methanation catalyst through which the feed gas flows and a space surrounding the tubes through which the water flows. By having the water flow through a space between the outside of the tubes and the inside of the reactor vessel instead of through the tubes, a more evenly distributed cooling can be achieved, avoiding cold-spots in the internally cooled methanation reactor. Also the heat control is improved as the distance across which the heat generated in the tubes needs to be transported is shorter than when a fixed bed or fluidized bed of catalyst is cooled by water flowing in a system of tubes. It further allows one to avoid high temperatures for the reactor walls.

The internally cooled methanation reactor may be vertically oriented or horizontally oriented. Preferably the internally cooled methanation reactor is vertically oriented. In such a vertically oriented internally cooled reactor the flow of the feed gas may be bottom-up or top-down. Preferably the flow of the feed gas is top-down.

In a further preferred embodiment the internally cooled methanation reactor is a multitubular reactor. Such a multitubular reactor preferably comprises a substantially vertically extending vessel, a plurality of open-ended reactor tubes arranged in the vessel parallel to its central longitudinal axis, supply means for supplying the feed gas to a top fluid chamber and an effluent outlet arranged in a bottom fluid chamber. Preferably the upper ends of the open-ended reactor tubes are fixed to an upper tube plate and in fluid communication with the top fluid chamber above the upper tube plate and the lower ends of the open-ended reactor tubes are fixed to a lower tube plate and in fluid communication with the bottom fluid chamber below the lower tube plate. The number of tubes in the multitubular reactor can vary within a wide range and also depends on the desired capacity. For practical purposes a number of tubes in the range from 10 to 20,000 is preferred and a number of tubes in the range of 100 to 10,000 is more preferred.

The internal diameter of the tubes should be small enough to allow a sufficient transfer of reaction heat to the water for cooling and large enough to avoid unnecessary material costs. The optimal diameter of the reactor tubes depends the amount of reactants and the catalyst used. In the process of the present invention reactor tube internal diameters in the range of 10 to 100 mm are preferred and reactor tube internal diameters in the range from 20 to 70 mm are more preferred.

The internally cooled methanation reactor may comprise one or more methanation catalysts. The nickel comprising methanation catalyst may be any nickel comprising methanation catalyst known to be suitable for this purpose. In addition to nickel the catalyst may optionally comprise molybdenum, cobalt and/or ruthenium. The methanation catalyst may comprise a carrier, which carrier may comprise for example alumina, silica, magnesium, zirconia or mixtures thereof. Preferably the nickel comprising catalyst is a catalyst comprising in the range from 10 wt % to 60 wt % nickel and more preferably in the range from 10 wt % to 30 wt % nickel.

Any catalyst may be present in the internally cooled reactor in any form known to be suitable by the skilled person. The catalyst(s) may be present as a fixed bed or fluidized bed, the catalyst may be packed in a tubes present in the reactor, or the catalysts may be coated on granules packed in a reactor or coated on for example a tubular or spiral structure within the reactor.

Preferably the feed gas is fed into the internally cooled methanation reactor at a temperature in the range from 200° C. to 500° C., preferably in the range from 250° C. to 400° C., and more preferably in the range from 260 to 300° C. and a pressure in the range from 10 to 60 bar, preferably in the range from 20 to 50 bar, more preferably in the range from 25 to 45 bar. The flowrate of the gas mixture into the internally cooled methanation reactor, on the basis of a plant producing 14.1 million standard cubic meters of methane-containing product gas per day, is preferably equal to or less than 150 Kmol/sec and preferably at least 10 Kmol/sec.

The feed gas can flow through the internally cooled methanation reactors in a direction cross-currently, co-currently or counter-currently to the stream of water. Preferably the feed gas flows through the internally cooled methanation reactors in a direction counter-currently to the direction in which the water flows through the internally cooled methanation reactor.

The water enters the internally cooled methanation reactor at temperature in the range from 20-120° C. below the boiling temperature, preferably at a temperature in the range from 30-110° C. below its boiling temperature, and more preferably at a temperature in the range from 50-100° C. below its boiling temperature. Preferably the water enters the internally cooled methanation reactor at a temperature below 275° C., more preferably at a temperature in the range from 200° C. to 270° C.

The water is preferably fed to the internally cooled methanation regions at a pressure in the range from 50 bar to 150 bar, preferably from 60 bar to 125 bar.

In the internally cooled methanation reaction the water is subsequently heated to a higher temperature. Preferably the water is heated in the internally cooled methanation reactor to its to boiling temperature to produce steam. The water leaving the internally cooled reactor may for example be completely vaporized or partly vaporized, that is, the heated water may leave the internally cooled reactor as vapour or a liquid/vapour mixture.

Preferably the process according to the invention is carried out in a series of methanation reactors, which series comprises the internally cooled methanation reactor described above and one or more additional methanation reactor(s). The additional methanation reactor(s) may comprise one or more additional internally cooled methanation reactors, one or more adiabatic methanation reactors or a combination of internally cooled methanation reactor(s) and adiabatic methanation reactor(s). The additional methanation reactors may contain the same or a different methanation catalyst than the above described internally cooled methanation reactor comprising the nickel containing methanation catalyst.

Preferably the process according to the invention is a process that co-produces methane and superheated steam which comprises reacting the feed gas containing carbon monoxide and hydrogen in a series of at least two methanation reactors comprising at least one internally cooled methanation reactor containing a nickel comprising methanation catalyst to produce the product gas containing methane;

cooling the internally cooled methanation reactor with water, wherein the water enters the internally cooled methanation reactor at a temperature in the range from 20-120° C. below its boiling temperature and wherein the water is heated in the internally cooled methanation reactor to its boiling temperature to produce steam, and superheating steam produced in the internally cooled methanation reactor with heat generated in one or more of the other methanation reactors to produce superheated steam.

The process can for example use a total of two, three, four or five methanation reactors. Preferably a series of two or three methanation reactors are used.

The one or more other methanation reactors may comprise one or more other internally cooled methanation reactors and/or one or more adiabatic methanation reactors. The produced steam may for example be superheated in another internally cooled methanation reactor or in a heat exchanger situated directly downstream of an adiabatic methanation reactor, where the heat generated in the adiabatic methanation reactor can be used.

Preferably the first methanation reactor in the series of methanation reactors is an internally cooled reactor. More preferably the series of methanation reactors comprises only internally cooled methanation reactors, that is, preferably any other methanation reactors present are internally cooled methanation reactors.

The other internally cooled methanation reactors may be the same or different from the above internally cooled methanation reactor. Preferably, however, all internally cooled methanation reactors comprise tubes filled with a nickel comprising methanation catalyst and a space surrounding the tubes where the water flows through the space surrounding the tubes.

In a preferred embodiment the internally cooled methanation reactor and/or, if present, one or more of the other methanation reactors may contain a water-gas shift catalyst in addition to the methanation catalyst.

The water-gas shift catalyst may be any catalyst known to be suitable for such purpose as described above.

When present, the water-gas shift catalyst is preferably present as a mere separate layer of water-gas shift catalyst, located upstream of a methanation catalyst. When the water-gas shift catalyst is present upstream of the methanation catalyst, the feed gas to the methanation reactor first passes the water-gas shift catalyst before coming into contact with the methanation catalyst.

The presence of such a water-gas shift catalyst is most advantageous in the first or most upstream methanation reactor. Without wishing to be bound by any kind of theory, it is believed that the water-gas shift catalyst advantageously allows water and carbon monoxide in the feed gas to react thereby generating heat, which allows the feed gas to increase quickly in temperature to a temperature high enough for the methanation reaction to initiate. For example, such a water-gas shift reaction may quickly increase the temperature of the (shifted) feed gas to a temperature above 300° C. but below 400° C.

In a further preferred embodiment the internally cooled methanation reactor and/or, if present, one or more of the other methanation reactors may comprise an empty area not comprising any catalyst through which the feed gas flows. For example the tubes in an internally cooled methanation reactor may comprises a first area, that comprises catalyst, and a second area, upstream of the first area, that does not comprise any catalyst. The second area that does not comprise any catalyst can be used to preheat a flow of gas before it is contacted with the catalyst in the first area.

In addition to superheating the produced steam with heat generated in one or more of the other methanation reactors, other sources of heat can be used to superheat the produced steam. For example heat generated in a gasification process when cooling raw synthesis gas, or heat generated during a high temperature water-gas shift may be used as additional sources of heat to superheat the produced steam.

Preferably the steam produced in the internally cooled methanation reactor is stored in a steam separation vessel before being superheated. As the water may contain dissolved mineral matter (for example iron, calcium or magnesium oxides) that could accumulate in the steam separation vessel, the steam separation vessel preferably comprises a bleed stream through which mineral matter can be removed. With the help of such a bleed stream the concentration of mineral matter can be kept below any level at which precipitation may occur. Such bleed stream can further be advantageous to control the liquid/vapour ratio in the steam separation vessel when this is desired.

For practical purposes, the bleed stream preferably comprises less than 1 wt % of the total water flow rate.

If it is necessary to add liquid water to the steam separation vessel, such liquid water may conveniently be obtained from flash-drums used to knock out water upstream or downstream of the methanation reactors.

The produced superheated steam may be used for any purpose known by the person skilled in the art. For example the superheated steam may be used to generate power.

In a preferred embodiment at least part of the steam or superheated steam produced is added to the feed gas to reduce coke formation in the methanation reactors.

In another preferred embodiment at least part of the steam or superheated steam produced is used in a gasification reaction to produce synthesis gas. The steam or superheated steam may for example be used as a temperature moderator in the gasification reaction, to generate power for the gasification reaction or to preheat the reactants for the gasification reaction.

The process according to the invention produces a product gas containing methane. In addition to methane the product gas may contain other compounds such as carbon dioxide, water, unreacted carbon monoxide, unreacted hydrogen, nitrogen and/or argon.

The product gas preferably has a temperature in the range from 250 to 350° C., more preferably a temperature in the range from 275 to 325° C. In a preferred embodiment the product gas is used to preheat the feed gas and/or the cooling water. In such manner a most advantageous heat integration is obtained.

The product gas containing methane may subsequently be purified by any method known in the art to increase the methane content in the product gas. The optionally purified, product gas containing methane can be used as a substitute for natural gas.

Figure 1:
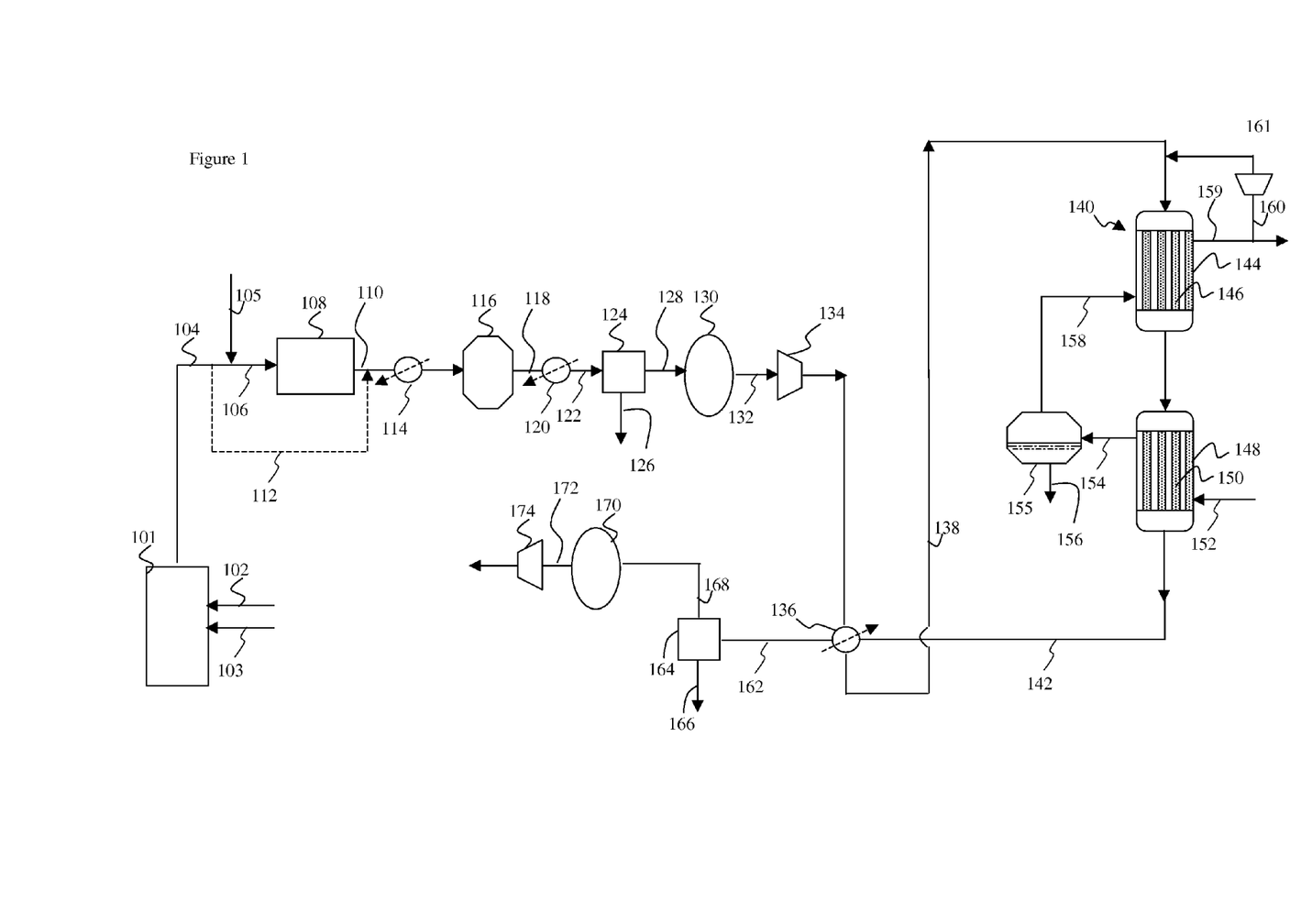
FIG. 1 schematically shows a first process according to the invention.
Figure 3:
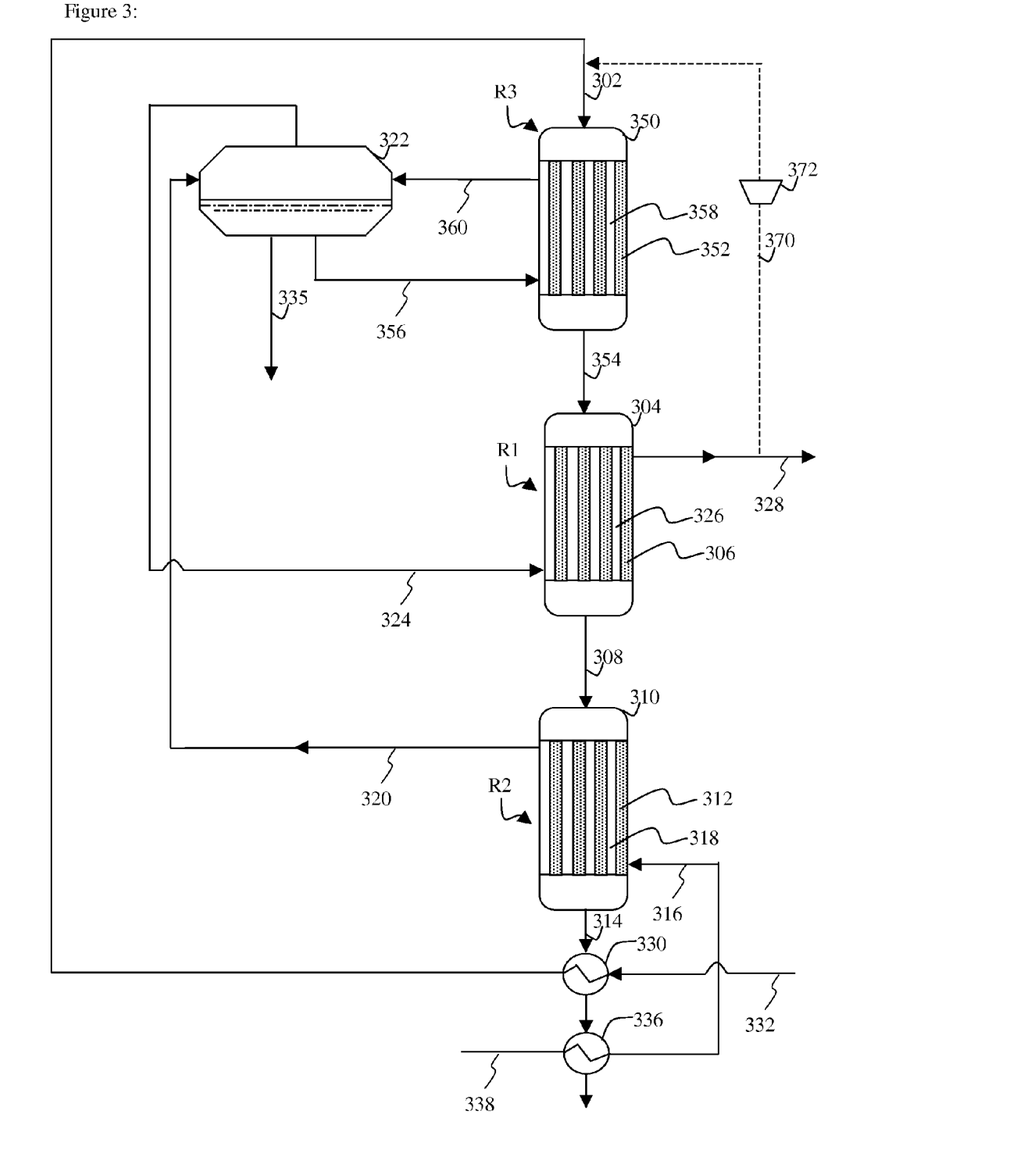
FIG. 3 schematically shows a third process according to the invention.
Figure 4:
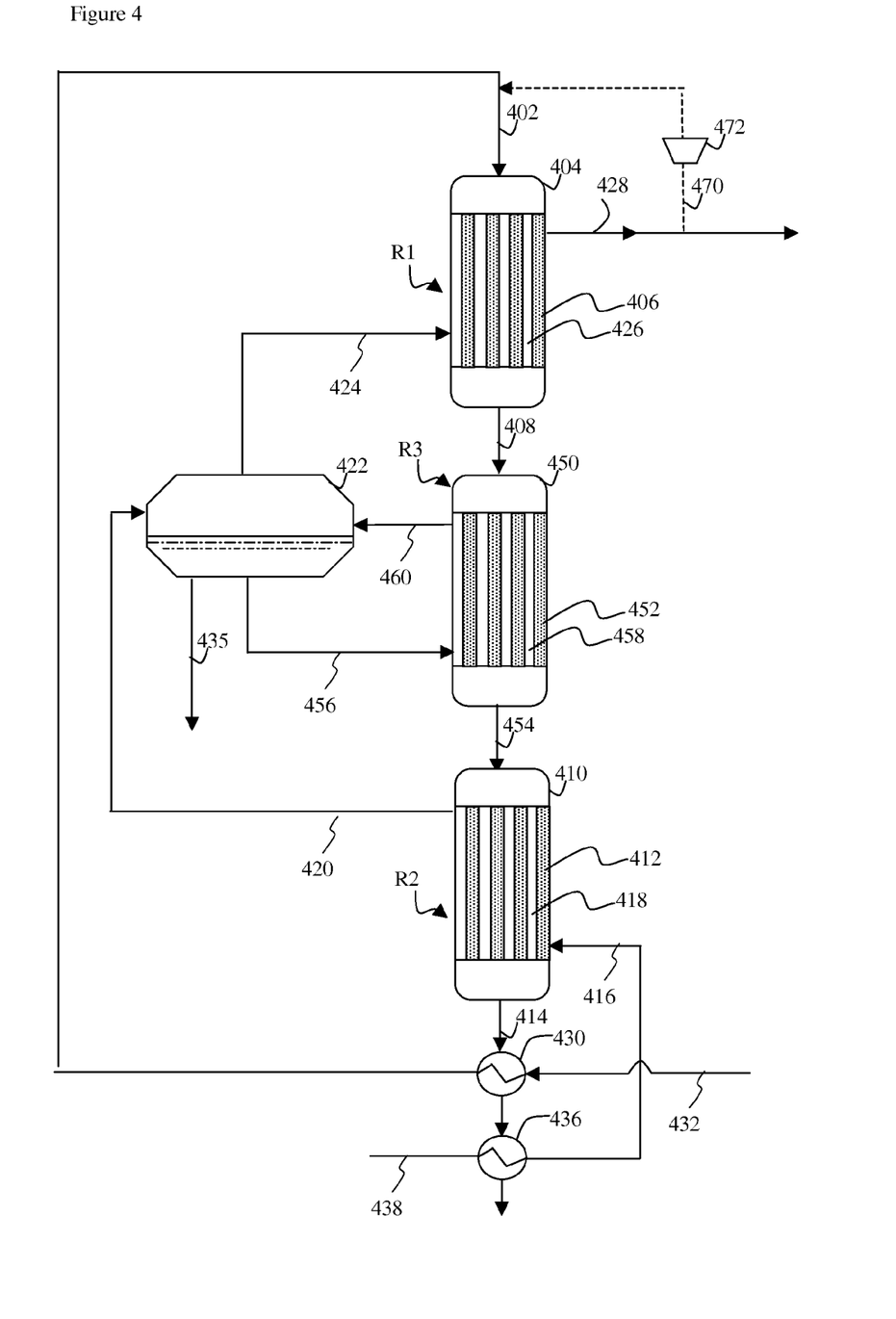
FIG. 4 schematically shows a fourth process according to the invention.

In FIG. 1, one example of a process according to the invention is shown. In a coal gasification unit (101) a stream of coal (102) is oxidized with an oxygen containing stream (103) to produce a synthesis gas stream (104). The synthesis gas stream (104) comprises carbon monoxide and hydrogen, and may in addition optionally comprise some water and carbon dioxide. The synthesis gas stream (104) is combined with a steam stream (105) to provide a water gas shift feed stream (106). The water gas shift feed stream (106) is forwarded to a high temperature water-gas shift reactor (108) at a temperature of about 300-350° C. and leaves the high temperature water-gas shift reactor at a temperature of about 550° C. In the high temperature water-gas shift reactor, steam and the carbon monoxide react to produce a shifted synthesis gas stream (110), comprising a higher ratio of hydrogen to carbon monoxide. The shifted synthesis gas stream (110) may optionally be mixed with a stream of non-shifted synthesis gas (112). The shifted synthesis gas stream (110) is cooled in a heat exchanger (114) and subsequently desulphurized in a desulphurization unit (116) to produce a desulphurized synthesis gas stream (118). The desulphurized synthesis gas stream (118) is cooled down further in a heat exchanger (120), after which a cooled desulphurized synthesis gas stream (122) is forwarded to a flash drum (124) to remove water. In the flash drum (124) water is knocked out and removed via stream (126). The resultant stream (128) is forwarded to a carbon dioxide removal unit (130), where carbon dioxide is removed. The carbon dioxide removal unit (130) produces a stream (132) comprising a cooled and dried carbon dioxide-lean synthesis gas that can be used as a feed gas to an internally cooled methanation reactor. The stream (132) of such feed gas is compressed in compressor (134) and preheated in heat-exchanger (136) to produce a stream of feed gas (138) with a temperature in the range from 270° C. and 300° C. and a pressure of about 35 bar. The stream of feed gas (138) is forwarded to a series of methanation reactors (140), comprising at least two internally cooled methanation reactors. In the series of methanation reactors a stream of product gas (142) containing methane is produced. In FIG. 1, a series of a first internally cooled methanation reactor (144) containing a nickel containing methanation catalyst (146) and a second internally cooled methanation reactor (148) containing a nickel containing methanation catalyst (150) is illustrated. As illustrated in FIGS. 3 and 4 hereafter, however, the series of methanation reactors can for example also comprise three internally cooled methanation reactors containing a methanation catalyst.

The first internally cooled methanation reactor (144) and the second internally cooled methanation reactor (148) are cooled with water. A stream of liquid water (152) is heated in the second internally cooled methanation reactor (148) from a temperature of 232° C. at a pressure of 78 bar to its boiling temperature at 78 bar (i.e. 293° C.) to produce a stream comprising steam and water (154). The steam and water from stream (154) are collected in steam separation vessel (155) comprising a bleed stream (156). Subsequently a further stream comprising only steam (158) is withdrawn from the steam separation vessel (155) and superheated in the first internally cooled methanation reactor (144) to produce a stream comprising superheated steam (159). A stream (160) comprising part of the superheated steam may be split from stream (159). This stream (160) may be used to generate power in an expander (161) and may subsequently be added to the stream of feed gas (138) or elsewhere in the process (for example added to steam stream (105) or as a separate stream into coal gasification unit (101)).

The stream of product gas (142) is cooled in heat exchanger (136) and a stream (162) of cooled product gas is forwarded to a flash drum (164) to remove water. In the flash drum (164) water is knocked out and removed via stream (166) and a stream (168) comprising cooled and dried product gas is produced. Stream (168) is forwarded to a carbon dioxide removal unit (170), where carbon dioxide is removed from the cooled and dried product gas. The carbon dioxide removal unit (170) produces a final product stream (172) comprising cooled and dried carbon dioxide-lean product gas that may be brought to a desired pressure in compressor (174).

Figure 2:
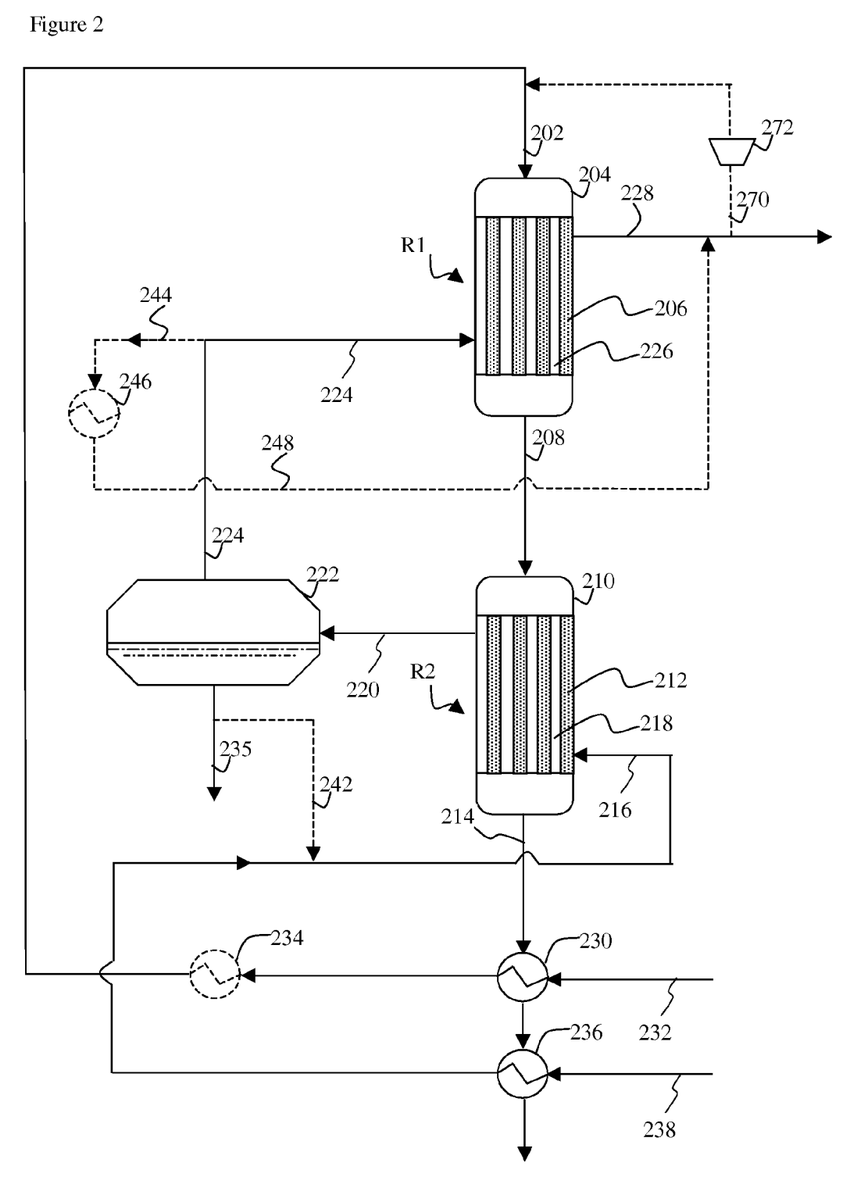
FIG. 2 schematically shows a second process according to the invention.

In FIG. 2, an example of a series of two internally cooled methanation reactors that can be used in the process of the invention is illustrated. A stream of feed gas comprising carbon monoxide and hydrogen, having a temperature in the range from about 270° C. to about 300° C., enters a first internally cooled methanation reactor (204, R1 in the figure) comprising multiple tubes containing a nickel-based methanation catalyst (206) via line (202). In the first internally cooled methanation reactor (204) the carbon monoxide and hydrogen are partially converted and a stream of an intermediate product gas comprising methane and unreacted carbon monoxide and hydrogen, having a temperature of about 320° C., leaves the internally cooled methanation reactor (204) via a line (208) connecting the first internally cooled reactor (204) with a second internally cooled reactor (210, R2 in the figure). The intermediate product stream is subsequently fed into the second internally cooled reactor (210) comprising multiple tubes containing a nickel-based methanation catalyst (212). In the second internally cooled reactor (210) at least part of the remaining carbon monoxide and hydrogen react and a stream of a product gas comprising methane, having a temperature of about 300° C., leaves the second internally cooled reactor (210) via a line (214).

The first internally cooled reactor (204) and the second internally cooled reactor (210) are cooled by a flow of water. In the embodiment shown in FIG. 2, the water enters the second internally cooled reactor (210) at the bottom via line (216) at a temperature of 232° C. and a pressure of 78 bar, that is at a temperature 61° C. below the boiling temperature at that pressure (293° C.). In the second internally cooled reactor (210) the water cools the tubes (212) by flowing through a space (218) surrounding the tubes (212). The water flows in such space (218) in a direction counter currently to the direction of the gas flow in the tubes (212). In the second internally cooled reactor (210) the water is heated to its boiling temperature of 293° C. The water leaves the second internally cooled reactor (210) from the top via line (220) as heated water in a mixed liquid/vapor phase. The heated water is forwarded to a steam separation vessel (222). Steam is withdrawn from the steam separation vessel (222) via line (224) and fed into the bottom of the first internally cooled reactor (204) at a temperature of 293° C. and a pressure of 78 bar. The steam cools the tubes (206) in the first internally cooled reactor (204) by flowing through the space (226) surrounding the tubes (206). The steam flows in such space (226) in a direction counter currently to the direction of the gas flow in the tubes (206). In the first internally cooled reactor (204) the steam is superheated to a temperature of 450° C. at a pressure of 78 bar and leaves the first internally cooled reactor (204) as superheated steam via line (228).

The process of FIG. 2 allows a good conversion in the last part of the second internally cooled reactor whilst deactivation of the nickel containing methanation catalyst is minimized.

In the embodiment of FIG. 2, the stream of product gas in line (214) is advantageously cooled in a heat exchanger (230) by a stream of feed gas of 40° C. (232) whilst this stream of feed gas of 40° C. (232) is simultaneously heated to a desired temperature in the range from about 270° to about 300° C. for feeding via line (202) to the first internally cooled methanation reactor (204). Optionally the stream of feed gas that has been preheated in heat exchanger (230) may be heated further in a second heat exchanger (234) by using other sources of heat, for example heat generated in a high temperature shift reactor.

In addition the product gas in line (214) may advantageous be cooled in a heat exchanger (236) by a stream of water of 40° C. (238) whilst this stream of water of 40° C. (238) is simultaneously heated to a desired temperature below 275° C. for feeding via line (216) to the second internally cooled methanation reactor (210). The steam separation vessel (222) preferably comprises a bleed stream (235) to remove any mineral matter in the water streams that might have accumulated in the steam separation vessel (222). In the embodiment of FIG. 2, the bleed stream (235) may further advantageously be used to control the amount of liquid water in the steam separation vessel (222). Depending on the flow rate of the water and the temperatures inside the second internally cooled reactor (210), stream (220) may comprise a higher or lower ratio of liquid water to steam. By variation of the size of the bleed stream it becomes possible to adjust for an excess or shortage of liquid water in stream (220). In addition, water may optionally be split off from bleed stream (235) and redirected via line (242) to line (216) to assist in controlling of the amount of liquid water in steam separation vessel (222).

In addition to superheating steam withdrawn from the steam separation vessel (222) in the first internally cooled reactor (204), part of the steam in line (224) withdrawn from the steam separation vessel (222) may be split off via line (244) and superheated in a heat exchanger (246) by heat generated elsewhere in the process, for example, by heat generated in a high temperature shift reactor. The generated stream of superheated steam (248) can be combined with the superheated steam stream (228) generated in the first internally cooled reactor (204).

A part of the superheated stream generated may be split off via line (270) and may be used to generate power in an expander (272) and/or may be added to the feed gas in line (202) to prevent coking in the methanation reactors.

In FIG. 3, a third example of a process according to the invention is shown. The process of FIG. 3 is similar to that of FIG. 2, except that a third internally cooled reactor (350, R3 in FIG. 3) has been positioned before the first internally cooled reactor (304) and the second internally cooled reactor (310). A stream of feed gas (302) comprising carbon monoxide and hydrogen enters this third internally cooled methanation reactor (350) comprising multiple tubes containing a nickel-based methanation catalyst (352). In the third internally cooled methanation reactor (350) the carbon monoxide and hydrogen are partially converted and a first stream (354) of a first intermediate product gas comprising methane and unreacted carbon monoxide and hydrogen leaves the third internally cooled methanation reactor (350) and is forwarded to the first internally cooled reactor (304) comprising multiple tubes containing a nickel-based methanation catalysts (306). In the first internally cooled reactor (304) part of the remaining carbon monoxide and hydrogen in the first intermediate product gas react and a stream of a second intermediate product gas (308) comprising methane leaves the first internally cooled reactor and is forwarded to the second internally cooled reactor (310) comprising multiple tubes containing a nickel-based methanation catalyst (312). In the second internally cooled reactor (310) at least part of the remaining carbon monoxide and hydrogen react and a stream of a product gas comprising methane leaves the second internally cooled reactor (310) via a line (314).

The first internally cooled reactor (304), the second internally cooled reactor (310) and the third internally cooled reactor (350) are cooled by a flow of water. In the embodiment shown in FIG. 3, the water enters the second internally cooled reactor (310) at the bottom via line (316) at a temperature of 232° C. and a pressure of 78 bar, that is at a temperature 61° C. below the boiling temperature at that pressure (293° C.). The water cools the tubes (312) in the second internally cooled reactor (310) by flowing through a space (318) surrounding the tubes (312). The water flows in such space (318) in a direction counter currently to the direction of the gas flow in the tubes (312). In the second internally cooled reactor (310) the water is heated to its boiling temperature of 293° C. The water leaves the second internally cooled reactor (310) from the top via line (320) as heated water in a mixed liquid/vapor phase. The heated water is stored in a steam separation vessel (322). Liquid water is withdrawn from the steam separation vessel (322) via a line (356) and fed into the bottom of the third internally cooled reactor (350). The water cools the tubes (352) in the third internally cooled reactor (350) by flowing through the space (358) surrounding the tubes (352). The water flows in such space (358) in a direction counter currently to the direction of the gas flow in the tubes (352). In the third internally cooled reactor (350), the liquid water of 293° C. and pressure of 78 bar is partially converted to steam of 293° C. and 78 bar. Steam and water leave the third internally cooled reactor via a line (360) and flow back into the steam separation vessel (322).

Steam is withdrawn from the steam separation vessel (322) via line (324) and fed into the bottom of the first internally cooled reactor (304) at a temperature of 293° C. and a pressure of 78 bar. The steam cools the tubes (306) in the first internally cooled reactor (304) by flowing through the space (326) surrounding the tubes (306). The steam flows in such space (326) in a direction counter currently to the direction of the gas flow in the tubes (306). In the first internally cooled reactor (304) the steam is superheated to a temperature of 450° C. at a pressure of 78 bar and leaves the first internally cooled reactor (304) as superheated steam via line (328).

In the embodiment of FIG. 3, the stream of product gas in line (314) is advantageously cooled in a heat exchanger (330) by a stream of feed gas of 40° C. (332) whilst this stream of feed gas of 40° C. (332) is simultaneously heated to a desired temperature in the range from about 270° to about 300° C. for feeding via line (302) to the third internally cooled methanation reactor (350).

In FIG. 4, a fourth example of a process according to the invention is shown. The process of FIG. 4 is similar to that of FIG. 2, except that a third internally cooled reactor (450, R3 in FIG. 4) has been positioned between the first and the second internally cooled reactor. A stream of feed gas comprising carbon monoxide and hydrogen enters a first internally cooled methanation reactor (404) comprising multiple tubes containing a nickel-based methanation catalysts (406) via line (402). In the first internally cooled methanation reactor (404) the carbon monoxide and hydrogen are partially converted in the reactor and a first stream of a first intermediate product gas comprising methane and unreacted carbon monoxide and hydrogen leaves the internally cooled methanation reactor (404) via a line (408) connecting the first internally cooled reactor (404) with a third internally cooled reactor (450). The first intermediate product stream is subsequently fed into the third internally cooled reactor (450) comprising multiple tubes containing a nickel-based methanation catalyst (452). In the third internally cooled reactor (450) part of the remaining carbon monoxide and hydrogen in the first intermediate product gas react and a stream of a second intermediate product gas (454) comprising methane leaves the third internally cooled reactor (450). The second intermediate product stream (454) is subsequently fed into the second internally cooled reactor (410) comprising multiple tubes containing a nickel-based methanation catalyst (412). In the second internally cooled reactor (410) at least part of the remaining carbon monoxide and hydrogen react and a stream of a product gas comprising methane leaves the second internally cooled reactor (410) via a line (414).

The first internally cooled reactor (404), the second internally cooled reactor (410) and the third internally cooled reactor (450) are cooled by a flow of water. In the embodiment shown in FIG. 4, the water enters the second internally cooled reactor (410) at the bottom via line (416) at a temperature of 232° C. and a pressure of 78 bar, that is at a temperature 61° C. below the boiling temperature at that pressure (293° C.). The water cools the tubes (412) in the second internally cooled reactor (410) by flowing through a space (418) surrounding the tubes (412). The water flows in such space (418) in a direction counter currently to the direction of the gas flow in the tubes (412). In the second internally cooled reactor (410) the water is heated to its boiling temperature of 293° C. The water leaves the second internally cooled reactor (410) from the top via line (420) as heated water in a mixed liquid/vapor phase. The heated water is stored in a steam separation vessel (422). Liquid water is withdrawn from the steam separation vessel (422) via a line (456) and fed into the bottom of the third internally cooled reactor (450). The water cools the tubes (452) in the third internally cooled reactor (450) by flowing through the space (458) surrounding the tubes (452). The water flows in such space (458) in a direction counter currently to the direction of the gas flow in the tubes (452). In the third internally cooled reactor (450), the liquid water of 293° C. and pressure of 78 bar is partially converted to steam of 293° C. and 78 bar. Steam and water leave the third internally cooled reactor via a line (460) and flow back into the steam separation vessel (422).

Steam is withdrawn from the steam separation vessel (422) via line (424) and fed into the bottom of the first internally cooled reactor (404) at a temperature of 293° C. and a pressure of 78 bar. The steam cools the tubes (406) in the first internally cooled reactor (404) by flowing through the space (426) surrounding the tubes (406). The steam flows in such space (426) in a direction counter currently to the direction of the gas flow in the tubes (406). In the first internally cooled reactor (404) the steam is superheated to a temperature of 450° C. at a pressure of 78 bar and leaves the first internally cooled reactor (404) as superheated steam via line (428).

In the embodiment of FIG. 4, the stream of product gas in line (414) is advantageously cooled in a heat exchanger (430) by a stream of feed gas of 40° C. (432) whilst this stream of feed gas of 40° C. (432) is simultaneously heated to a desired temperature in the range from about 270° to about 300° C. for feeding via line (402) to the first internally cooled methanation reactor (404).

In the embodiments of respectively FIG. 3 and FIG. 4, the product gas in line (314) respectively (414) may advantageously be further cooled in a heat exchanger (336) respectively (436) by a stream of water of 40° C. (338) respectively (438) whilst this stream of water of 40° C. (338) respectively (438) is simultaneously heated to a desired temperature below 275° C. for feeding via line (316) respectively (416) to the second internally cooled methanation reactor (310) respectively (410).

Further a part of the superheated stream generated may be split off via line (370) respectively (470) and may be used to generate power in an expander (372) respectively (472) and/or may be added to the feed gas in line (302) respectively (402), to prevent coking in the methanation reactors, or elsewhere in the process where steam addition is needed.

The steam separation vessel (322) respectively (422) preferably comprises a bleed stream (335) respectively (435) to remove any solid material in the water streams that otherwise might have accumulated in the steam separation vessel (322) respectively (422).

What is claimed is:

1. A process for the production of methane comprising reacting at least part of a feed gas containing carbon monoxide and hydrogen in an internally cooled methanation reactor containing a nickel comprising methanation catalyst to produce a product gas containing methane, cooling the internally cooled methanation reactor with water, wherein the water enters the internally cooled methanation reactor at a temperature in the range from 20-120° C. below its boiling temperature.

2. The process according to claim 1, wherein the internally cooled reactor comprises tubes filled with the nickel comprising methanation catalyst and a space surrounding the tubes; and wherein the feed gas flows through the tubes and the water flows through the space surrounding the tubes.

3. The process according to claim 1, wherein the feed gas flows through the internally cooled methanation reactors in a direction counter-currently to the direction in which the water flows through the internally cooled methanation reactor.

4. The process according to claim 1, wherein the water enters the internally cooled methanation reactor at pressure in the range from 50 to 100 bar.

5. The process according to claim 1, wherein the water enters the internally cooled methanation reactor at a temperature below 275° C.

6. The process according to claim 1, wherein the process co-produces methane and superheated steam and the process comprises reacting the feed gas containing carbon monoxide and hydrogen in a series of at least two methanation reactors comprising at least one internally cooled methanation reactor containing a nickel comprising methanation catalyst to produce the product gas containing methane;

cooling the internally cooled methanation reactor with water, wherein the water enters the internally cooled methanation reactor at a temperature in the range from 20-120° C. below its boiling temperature and wherein the water is heated in the internally cooled methanation reactor to its boiling temperature to produce steam, and superheating steam produced in the internally cooled methanation reactor with heat generated in one or more of the other methanation reactors to produce superheated steam.

7. The process according to claim 6, wherein the series of methanation reactors comprises one or more adiabatic methanation reactors in addition to the internally cooled methanation reactor.

8. The process according to claim 6, wherein the series of methanation reactors comprises only internally cooled methanation reactors.

9. The process according to claim 6, further comprising storing steam produced in the internally cooled methanation reactor in a steam separation vessel and retrieving the produced steam from the steam separation vessel to produce superheated steam.

10. The process according to claim 6, wherein at least part of the produced steam and/or at least part of the produced superheated steam is added to the feed gas.

11. The process according to claim 6, wherein at least part of the produced steam and/or at least part of the produced superheated steam is used as a moderator in a gasification reaction to produce synthesis gas.

12. The process according to claim 1, further comprising the use of the product gas containing methane as a substitute for natural gas.

13. The process according to claim 1, wherein the feed gas is synthesis gas obtained by reacting a carbonaceous feed and an oxidant in a gasification reaction.

14. The process according to claim 12, wherein the carbonaceous feed comprises coal or petroleum coke.

* * * * *